US00PP23115P2

(12) United States Plant Patent

Klemm et al.

(10) Patent No.: US PP23,115 P2

(45) Date of Patent: Oct. 16, 2012

(54) *PELARGONIUM* PLANT NAMED 'KLEPZ10234'

(50) Latin Name: *Pelargonium zonale*
Varietal Denomination: KLEPZ10234

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 29 days.

(21) Appl. No.: 13/065,520

(22) Filed: Mar. 23, 2011

(51) Int. Cl.
*A01H 5/00* (2006.01)

(52) U.S. Cl. ..... Plt./328

(58) Field of Classification Search ..... Plt./325, Plt./328

See application file for complete search history.

*Primary Examiner* — Susan McCormick Ewoldt

(74) *Attorney, Agent, or Firm* — Jondle & Associates, P.C.

(57) ABSTRACT

A new variety of *Pelargonium* named 'KLEPZ10234', particularly characterized by shiny pink-colored flowers with white centers, good medium growth, dark foliage, and strong zonated leaves, is disclosed.

1 Drawing Sheet

Genus and species: *Pelargonium zonale.*
Variety denomination: 'KLEPZ10234'.

BACKGROUND OF THE NEW PLANT

The present invention comprises a new and distinct variety of *Pelargonium*, botanically known as *Pelargonium zonale*, and hereinafter referred to by the variety name 'KLEPZ10234'. The new variety is the result of a controlled cross conducted in June 2004 in Stuttgart, Germany between the proprietary female *Pelargonium* parent, 'SI-AN 02' (unpatented), and the proprietary male *Pelargonium* parent, 'KLEP01007' (U.S. Plant Pat. No. 13,763). A single plant selection was subsequently chosen for further evaluation and asexual propagation.

The new variety was first propagated via vegetative cuttings in September 2005 in Stuttgart, Germany and has been asexually reproduced repeatedly by vegetative cuttings in Stuttgart, Germany for approximately six to eight generations. 'KLEPZ10234' has been found to retain its distinctive characteristics through successive asexual propagations via vegetative cuttings.

Plant Breeder's Rights for this variety were applied for in the following countries: Canada on Mar. 30, 2010, Switzerland on Jun. 29, 2010, the European Union on Jul. 9, 2010, and Norway on Sep. 15, 2010. 'KLEPZ10234' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Shiny pink-colored flowers with white centers;
2. Good medium growth;
3. Dark foliage; and
4. Strong zonated leaves.

DESCRIPTION OF THE PHOTOGRAPH

This new *Pelargonium* plant is illustrated by the accompanying photograph which shows blooms, buds, and foliage of the plant. The colors shown are as true as can be reasonably obtained by conventional photographic procedures.

The photograph is of a 3-month old plant taken in Spring 2010 grown from a rooted cutting in a 12 centimeter pot in a glass greenhouse in Stuttgart, Germany under conditions which approximate those generally used in normal horticultural practice.

DESCRIPTION OF THE NEW VARIETY

The following detailed descriptions set forth the distinctive characteristics of 'KLEPZ10234'. The data which define these characteristics were collected from asexual reproductions carried out in Stuttgart, Germany. The plant history was taken on 3-month old, un-pinched plants grown in 12 centimeter pots in a glass greenhouse in Stuttgart, Germany. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Geraniaceae.
- *Species.*—*Pelargonium zonale.*
- *Common name.*—*Pelargonium* (Geranium).
- *Denomination.*—'KLEPZ10234'.

Parentage:
- *Female parent.*—The proprietary female *Pelargonium* parent, 'SI-AN 02' (unpatented).
- *Male parent.*—The proprietary male *Pelargonium* parent, 'KLEP01007' (U.S. Plant Pat. No. 13,763).

Plant:
- *Habit.*—Upright.
- *Height.*—22.0 cm to 25.0 cm.
- *Spread.*—Approximately 25.0 cm.
- *Life cycle.*—Spring to Fall.
- *Form.*—Round, bushy.
- *Time to produce a rooted cutting.*—17 days.

*Time to bloom from propagation.*—Approximately 102 days.

*Lastingness of inflorescence on the plant.*—16 days.

Stems:

*Stem color.*—RHS 137C.

*Pubescence.*—Yes, short.

*Stem form.*—Upright.

*Diameter.*—0.7 cm to 0.9 cm.

*Length.*—12.0 cm to 14.0 cm.

*Internode length.*—0.6 cm to 1.5 cm.

Leaves:

*Arrangement.*—Alternate.

*Shape.*—Round-closed.

*Apex.*—Round.

*Base.*—Closed.

*Margin.*—Crenated.

*Surface texture (both upper and lower surfaces).*—Rough.

*Length.*—5.0 cm to 7.0 cm.

*Width.*—5.0 cm to 7.0 cm.

*Color.*—Upper surface: RHS 137A. Lower surface: RHS 137C.

*Fragrance.*—Absent.

*Surface pubescence.*—Absent.

*Petiole.*—Length: 5.0 cm to 8.0 cm. Color: RHS 137C.

*Venation pattern.*—Palmate.

*Venation color.*—RHS 137D.

Inflorescence:

*Flowering habit.*—Continuously.

*Umbels.*—Length: 6.0 cm to 8.0 cm. Diameter: 7.0 cm to 9.0 cm.

*Individual florets of the umbel.*—Depth: 1.5 cm. Diameter: 3.0 cm.

Flower buds:

*Cluster shape.*—Round.

*Cluster size.*—Length: 4.5 cm. Width: 4.5 cm.

*Bud.*—Shape: Ovate. Apex: Picked. Base: Obtuse. Margin: Plane, entire. Color: RHS 137C and RHS 178A.

*Corolla.*—Diameter: 3.0 cm. Depth: 1.2 cm.

Petals:

*Quantity per flower.*—6 to 8.

*Shape.*—Spatulate.

*Apex.*—Round, entire.

*Base.*—Obtuse.

*Margin.*—Entire.

*Length.*—1.8 cm to 2.2 cm.

*Width.*—1.7 cm to 1.8 cm.

*Color of lobes.*—Upper lobes (both upper and lower surfaces): RHS 67C and RHS 69D. Lower lobes (both upper and lower surfaces): RHS N66C.

*Corolla tube color.*—Inner surface: RHS 67C and RHS 36D. Outer surface: RHS N66C.

*Fragrance.*—Absent.

Sepals:

*Number per flower.*—5.

*Shape.*—Elliptic.

*Apex.*—Picked.

*Base.*—Obtuse.

*Margin.*—Entire.

*Color (upper surface).*—RHS 137B.

*Length.*—0.6 cm to 0.8 cm.

*Width.*—0.2 cm to 0.4 cm.

Pedicel:

*Length.*—1.5 cm to 2.0 cm.

*Diameter.*—0.15 cm.

*Color.*—RHS 178B and RHS 138B.

Peduncle:

*Length.*—8.0 cm to 13.0 cm.

*Diameter.*—0.4 cm to 0.5 cm.

*Color.*—RHS 178A to RHS 178B and RHS 138B.

Reproductive organs:

*Stamens.*—Anther length: 0.15 cm. Filament length: 0.4 cm. Filament color: RHS 63D. Pollen amount: Moderate. Pollen color: RHS 35A.

*Pistils.*—Number: 1. Stigma color: RHS 63B. Style length: 0.2 cm. Style color: RHS 63D. Ovary arrangement: Upright.

Fruit and seed set: None observed.

COMPARISON WITH PARENTAL AND COMMERCIAL VARIETIES

'KLEPZ10234' differs from the female parent, 'SI-AN 02', in that 'KLEPZ10234' has pink flowers with white centers and a medium growth habit, while 'SI-AN 02' has light pink flowers and a strong growth habit.

'KLEPZ10234' differs from the male parent, 'KLEP01007', in that 'KLEPZ10234' has pink flowers with white centers, while 'KLEP01007' has salmon pink flowers. In addition, 'KLEPZ10234' has a stronger growth habit than 'KLEP01007'.

'KLEPZ10234' differs from the commercial comparison variety 'Mona Lisa' (unpatented), in that 'KLEPZ10234' has pink flowers with white centers and strong zonated leaves, while 'Mona Lisa' has salmon colored flowers with purple eyes and very weak zonated leaves.

We claim:

1. A new and distinct variety of *Pelargonium* plant named 'KLEPZ10234' as shown and described herein.

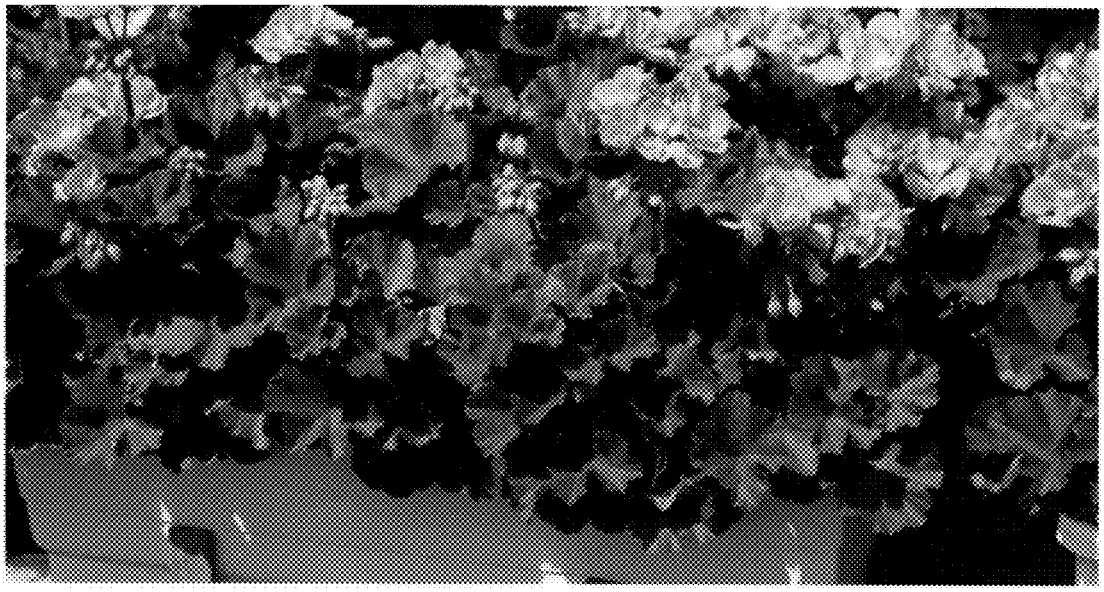

* * * * *